(12) United States Patent
Bauer et al.

(10) Patent No.: US 6,713,285 B2
(45) Date of Patent: *Mar. 30, 2004

(54) CIRCULAR SITE-DIRECTED MUTAGENESIS

(75) Inventors: John C. Bauer, San Diego, CA (US); Dowain A. Wright, Cambridge, MA (US); Jeffrey Carl Braman, Carlsbad, CA (US); Raif S. Geha, Belmont, MA (US)

(73) Assignees: Stratagene, La Jolla, CA (US); Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/144,652

(22) Filed: May 10, 2002

(65) Prior Publication Data

US 2003/0032037 A1 Feb. 13, 2003

Related U.S. Application Data

(63) Continuation of application No. 09/274,383, filed on Mar. 23, 1999, now Pat. No. 6,391,548, which is a continuation of application No. 08/844,524, filed on Apr. 17, 1997, now Pat. No. 5,932,419, which is a continuation of application No. 08/567,881, filed on Dec. 8, 1995, now Pat. No. 5,789,166.

(51) Int. Cl.[7] .............................................. C12P 19/34
(52) U.S. Cl. ...................................................... 435/91.2
(58) Field of Search .................................. 435/91.2, 810

(56) References Cited

U.S. PATENT DOCUMENTS

| | | | |
|---|---|---|---|
| 4,683,195 A | * | 7/1987 | Mullis et al. ................... 435/6 |
| 5,436,149 A | | 7/1995 | Barnes ........................... 435/6 |

(List continued on next page.)

FOREIGN PATENT DOCUMENTS

| | | |
|---|---|---|
| WO | WO 93/12257 | 6/1993 |
| WO | WO 93/18175 | 9/1993 |

OTHER PUBLICATIONS

Barnes, *Proc. Natl. Acad. Sci. U.S.A.*, 91:2216–2220 (1994).
Cheng et al., *Proc. Natl. Acad. Sci. U.S.A.*, 91:5695–5699 (1994).

(List continued on next page.)

*Primary Examiner*—Kenneth R. Horlick
(74) *Attorney, Agent, or Firm*—Finnegan, Henderson, Farabow, Garrett & Dunner LLP

(57) ABSTRACT

The invention provides improved methods of introducing site-directed mutations into circular DNA molecules of interest by means of mutagenic primer pairs. The mutagenic primer pairs are also selected so as to be either completely complementary or partially complementary to each other, wherein the mutation site (or sites) is located within the region of complementarity. A mutagenic primer pair is annealed to opposite strands of a circular DNA molecule containing the DNA sequence to be mutagenized. After annealing, first and second mutagenized DNA strands, each incorporating a member of the mutagenic oligonucleotide primer pair is synthesized by a linear cyclic amplification reaction. After the linear cyclic amplification mediated synthesis step is completed, the reaction mixture is treated with a selection enzyme that digests the parental template strands. After the digesting step, a double-stranded circular DNA intermediate is formed. The double-stranded circular DNA intermediates is transformed in suitable competent host cells and closed circular double-stranded DNA corresponding to the parental template molecules, but containing the desired mutation or mutations of interest, may be conveniently recovered from the transformed cells. The invention also provide kits for site-directed mutagenesis in accordance with methods of the present invention.

12 Claims, 1 Drawing Sheet

U.S. PATENT DOCUMENTS

| | | | |
|---|---|---|---|
| 5,512,463 A | 4/1996 | Stemmer | 435/91.2 |
| 5,514,568 A | 5/1996 | Stemmer | 435/6 |
| 5,789,166 A | 8/1998 | Bauer et al. | 435/6 |
| 5,932,419 A | 8/1999 | Bauer et al. | 435/6 |

OTHER PUBLICATIONS

Deng et al., *Analytical Biochemistry*, 200:81–88 (1992).
Drusta et al., *Nucleic Acids Research*, 20:922 (1991).
Hultman et al., *Nucleic Acids Research*, 18:5107–5112 (1990).
Jones et al., Methods: A Companion to Methods in Enzymology, 2(1):2–10 (1991).
Kunkel, *Proc. Natl. Acad. Sci. U.S.A.*, 82:488–492 (1985).
Lai et al., *Nucleic Acids Research*, 21:3977–3980 (1993).
McClary et al., Biotechniques, 7(3):282–287 (1989).
Stemmer and Morris, *Bio Techniques*, 13:214–220 (1992).
Stemmer et al., *Bio Techniques*, 14:256–265 (1993).
Taylor et al., *Nucleic Acids Research*, 13:8765–8785 (1985).
Vilardaga et al., *Bio Techniques*, 18:604–606 (1995).
Watkins et al., *Bio Techniques*, 5:700–704 (1993).
Weiner et al., *Gene*, 126:35–41 (1993).
Weiner et al., *PCR Methods & Applications*, 4(3):s131–s136 (1994).
Weiner et al., *Gene*, 151(1):119–123 (1994).
Yao et al., *PCR Methods Appl.*, 1:205–207 (1992).
Supplementary European Search Report, dated Aug. 19, 2002.

* cited by examiner

CIRCULAR SITE-DIRECTED MUTAGENESIS

This application is a continuation of U.S. application Ser. No. 09/274,383, filed Mar. 23, 1999, U.S. Pat. No. 6,391,548, which is a continuation of U.S. application Ser. No. 08/844,524, filed Apr. 17, 1997, U.S. Pat. No. 5,932,419, which is a continuation of U.S. application Ser. No. 08/567,881, filed Dec. 8, 1995, U.S. Pat. No. 5,789,166. The contents of U.S. application Ser. No. 08/567,881, including any drawing figures or sequence listings, is being relied upon and is incorporated herein by reference herein.

FIELD OF INVENTION

The invention is in the field of molecular biology, more particularly, in the field of the site-specific mutagenesis.

BACKGROUND

Site-directed mutagenesis has proved to a remarkably useful tool in molecular biology. Polynucleotides having pre-determined sequences may now be designed at will. Polymerase chain reaction (PCR) and various other cyclic amplification reactions have been adapted for use in site-directed mutagenesis. Although site-directed mutagenesis through PCR (the polymerase chain reaction) is widely used, PCR based site-directed mutagenesis techniques, have several shortcomings.

Several problems exist when trying to perform site-directed mutagenesis on double-stranded DNA molecules. These problems include strand separation and selection against the parental (non-mutated) DNA. Efficient strand separation is important because in a typical site-directed procedure, a single polynucleotide primer containing the desired sequence alteration must compete with the much longer complementary strand for a hybridization site. Both physical and chemical methods for strand separation have been used. Physical methods include the attachment of the DNA strands to a solid phase, such as a plastic bead (Hall, et al. *Protein Eng.* 4:601 (1991); Hultman, et al. *Nucleic Acids Research* 18:5107–5112 (1990); Weiner, et al. *Gene* 126:35–41 (1993), or the use of heat as a denaturant (Landt, et al. *Gene* 96:125–128 (1990); Sugimoto *Analytical Biochemistry* 179.:309–311 (1989). Chemical methods for strand separation usually rely on increasing the pH of the solution containing the DNA duplex (Weiner, et al. *Gene* 126:35–41 (1993).

Following strand separation, the primer is annealed to the parental strand and used to initiate DNA replication. After replication a means must be used to reduce the parental plasmid DNA contribution of the heteroduplex before or after cell transformation. Both in vivo and in vitro methods have been developed for this reduction. In non-amplification based in vivo site-directed methods, the incorporation of dUTP into parental DNA during growth of the vector can be selected against in $dut^+$, $ung^+$ E. coli cells (Kunkel *Proc. Natl. Acad. Sci. (U.S.A.)* 82:488–492 (1985). In vitro methods for selection of the mutated strand include; i) unique restriction site elimination (Deng, et al. *Analytical Biochemistry* 200:81–88 (1992), ii), solid phase techniques (where the parental DNA remains attached to the solid phase; Hultman, et al. *Nucleic Acids Research* 18:5107–5112 (1990); Weiner, et al. *Gene* 126:35–41 (1993), and iii) incorporation of modified bases in the newly replicated DNA (Taylor et al. *Nucleic Acids Research* 13:8765–8785 (1985); Vandeyar, et al. *Gene* 65:129–133 (1988).

When PCR has been used for site-specific mutagenesis, a strand separation is accomplished during the high temperature denaturation step in the cycling reaction. Selection against the parental DNA is usually accomplished by decreasing the amount of starting template and increasing the number of rounds of cycling. This increase in the number of cycles has the adverse effect of increasing the rate of spontaneous second-site mutations, especially if an error-prone polymerase such as Taq DNA polymerase is used. In a typical experiment, the mutated fragment is often subcloned from one vector to another. Often, different antibiotic resistance markers are alternated or the mutated fragment is gel isolated. Descriptions of the use of the polymerase chain reaction (PCR) in site specific mutagenesis can be found in Hall, et al. *Protein Eng.* 4:601 (1991); Hemsley, et al. *Nucleic Acids Research* 17:6545–6551 (1989); Ho, et al. *Gene* 77:51–59 (1989); Hultman, et al. *Nucleic Acids Research* 18:5107–5112 (1990); Jones, et al. *Nature* 344:793–794 (1990); Jones, et al. *Biotechniques* 12:528–533 (1992); Landt, et al. *Gene* 96:125–128 (1990); Nassal, et al. *Nucleic Acids Research* 18:3077–3078 (1990); Nelson, et al. *Analytical Biochemistry* 180:147–151 (1989); Vallette, et al. *Nucleic Acids Research* 17:723–733 (1989); Watkins, et al. *Biotechniques* 15:700–704 (1993); Weiner, et al. *Gene* 126:35–41 (1993). Yao, et al. *PCR Methods and Applications* 1:205–207 (1992). The use of site-directed mutagenesis is also described in Weiner et al, *Gene* 151:1/9–123(1994).

Given the many different methods of site-directed mutagenesis that are in use, it is clear that no single technique currently available solves all of the problems associated with the site-directed mutagenesis. Given the state of the art, it is clearly of interest to provide researchers (both industrial and academic) with useful new methods of site-directed mutagenesis. To this end, the inventors have developed new techniques for site-direct mutagenesis that have an advantageous combination of features as compared to other techniques for site-directed mutagenesis. These useful features include:

(1) low secondary mutation frequency, (2) high mutation efficiency, and (3) a minimal number of steps, thereby permitting the generation of host cells containing the mutant sequences in less than 24 hours.

SUMMARY OF INVENTION

The subject invention provides improved methods of site-directed mutagenesis involving linear cyclic amplification reactions. The invention provides extremely simple and effective methods of efficiently introducing specific mutations of interest into a target DNA.

The invention provides methods of introducing site-directed mutations into circular DNA of interest by means of mutagenic primer pairs that are selected so as to contain at least one mutation site with respect to the target DNA sequence. The mutagenic primer pairs are also selected so as to be either completely complementary or partially complementary to each other, wherein the mutation site (or sites) is located within the region of complementarity of both mutagenic primers.

In the methods of the invention, a mutagenic primer pair is annealed to opposite strands of a circular DNA molecule containing the DNA sequence to be mutagenized. After annealing, first and second mutagenized DNA strands, each incorporating a member of the mutagenic primer pair, are synthesized by a linear cyclic amplification reaction. The first and second mutagenized DNA strands synthesized are of sufficient lengths for forming a double-stranded mutagenized circular DNA intermediate. In certain embodiments, DMSO may be included in the linear cyclic amplification reaction. In certain embodiments, DMSO is used at a concentration in the range of 5–10% by volume. The linear cyclic amplification reaction may be repeated for several cycles so as to generate a sufficient amount of first and second mutagenized DNA strands for subsequent manipulations. After the linear cyclic amplification mediated synthesis step is completed, the reaction mixture is treated with a selection enzyme that digests the parental template strands, thereby enriching the reaction mixture with respect to the concentration of first and second mutagenized DNA strands. The digestion step serves to digest parental strands that have annealed to the newly synthesized mutagenized DNA strands and parental strands that have annealed to one another. After the digestion step, the first and second mutagenized DNA strands are permitted to hybridize to one another so as to form double-stranded circular DNA intermediates. The double-stranded circular DNA intermediates are transformed into suitable competent host cells and closed circular double-stranded DNA containing the desired mutation or mutations of interest may be conveniently recovered from the transformed cells.

The template digesting step in the methods of the invention may be carried out in any of a variety of methods involving a selection enzyme. The selection enzyme, e.g., a restriction endonuclease, is an enzyme that digests parental polynucleotides and does not digest newly synthesized mutagenized polynucleotides. Either template polynucleotides prior to replication are modified or polynucleotides synthesized during replication are modified so that the selection enzyme preferentially catalyzes the digestion of the parent template polynucleotide. In one embodiment of the invention the polynucleotide for mutagenesis is dam methylated double-stranded DNA and the restriction enzyme used to digest parental polynucleotide strands is Dpn I.

Another aspect of the invention is to provide kits for site-directed mutagenesis with high efficiency. The subject kits contain reagents required for carrying the subject methods.

DEFINITIONS

Figure 1:
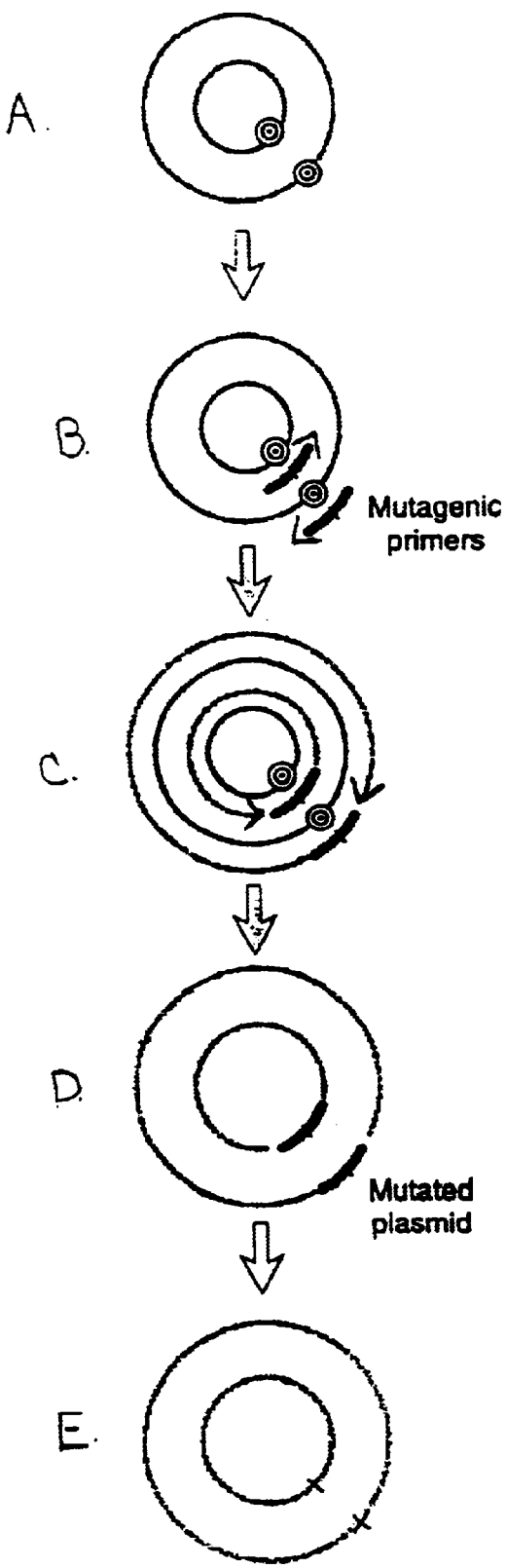
FIG. 1. This figure provides a schematic diagram of an embodiment of the subject methods of site-directed mutagenesis. Step (A) shows a circular closed double-stranded plasmid. The "bull's eye" symbol is used to indicate the target for mutagenesis. Step (B) shows the first and second mutagenic primer annealed to the circular closed double-stranded plasmid. The crosses indicate the mutagenic sites in the mutagenic primers. The arrows indicate the direction of synthesis. Step (C) shows the result of DNA synthesis from a linear cyclic amplification step. The lighter shaded circular regions represent newly synthesized DNA that is adjoined to the mutagenic primers. The arrows indicate the direction of synthesis. Step (D) shows the mutagenized DNA strands that remain after treatment with a selection enzyme. The first and second mutagenized strands are shown as being annealed to form a double-stranded mutagenized circular DNA intermediate. Note the nicks on each strand. Step (E) shows the resultant mutagenized circular double-stranded DNA molecules that are recovered after transforming competent cells with the double-stranded mutagenized circular DNA intermediate. Note that the crosses in the diagram reflect the mutagenized sites that correspond to the "bulls eyes" in Step (A).

The term 'linear cyclic amplification reaction,' as used herein, refers to a variety of enzyme mediated polynucleotide synthesis reactions that employ pairs of polynucleotide primers to linearly amplify a given polynucleotide and proceeds through one or more cycles, each cycle resulting in polynucleotide replication. Linear cyclic amplification reactions used in the methods of the invention differ significantly from the polymerase chain reaction (PCR). The polymerase chain reaction produces an amplification product that grows exponentially in amount with respect to the number of cycles. Linear cyclic amplification reactions differ from PCR because the amount of amplification product produced in a linear cyclic amplification reaction is linear with respect to the number of cycles performed. This difference in reaction product accumulation rates is a result of using mutagenic primers that are complementary or partially complementary to each other. A linear cyclic amplification reaction cycle typically comprises the steps of denaturing the double-stranded template, annealing primers to the denatured template, and synthesizing polynucleotides from the primers. The cycle may be repeated several times so as to produce the desired amount of newly synthesized polynucleotide product. Although linear cyclic amplification reactions differ significantly from PCR, guidance in performing the various steps of linear cyclic amplification reactions can be obtained from reviewing literature describing PCR including, PCR: A Practical Approach, M. J. McPherson, et al., IRL Press (1991), PCR Protocols: A Guide to Methods and Applications, by Innis, et al., Academic Press (1990), and PCR Technology: Principals and Applications of DNA Amplification, H. A. Erlich, Stockton Press (1989). PCR is also described in many U.S. Patents, including U.S. Pat. Nos. 4,683,195, 4,683,202; 4,800,159; 4,965,188; 4,889, 818; 5,075,216; 5,079,352; 5,104,792, 5,023,171; 5,091, 310; and 5,066,584, which are hereby incorporated by reference. In certain embodiments, DMSO may be included in the linear cyclic amplification reaction. In certain embodiments, DMSO is used at a concentration in the range of 5–10% by volume. Many variations of amplification techniques are known to the person of skill in the art of molecular biology. These variations include rapid amplification of DNA ends (RACE-PCR), amplification refectory mutation system (ARMS), PLCR (a combination of polymerase chain reaction and ligase chain reaction), ligase chain reaction (LCR), self-sustained sequence replication (SSR), Q-beta amplification, and stand displacement amplification (SDA), and the like. A person of ordinary skill in the art may use these methods to modify the linear cyclic amplification reactions used in the methods of the invention.

The term "mutagenic primer" refers to an oligonucleotide primer used in a linear cyclic amplification reaction, wherein the primer does not precisely match the target hybridization sequence. The mismatched nucleotides in the mutagenic primer are referred to as mutation sites with respect to the mutagenic primer. Thus, during the amplification reaction, the mismatched nucleotides of the primer are incorporated into the amplification product thereby resulting in the synthesis of a mutagenized DNA strand comprising the mutagenic primer that was used to prime synthesis mutagenizing the target sequence. The term "oligonucleotide" as used herein with respect to mutagenic primers is used broadly. Oligonucleotides include not only DNA but various analogs thereof. Such analogs may be base analogs and/or backbone analogs, e.g., phosphorothioates, phosphonates, and the like. Techniques for the synthesis of oligonucleotides, e.g., through phosphoramidite chemistry, are well known to the person ordinary skilled in the art and are described, among other places, in *Oligonucleotides and Analogues: A Practical Approach*, ed. Eckstein, IRL Press, Oxford (1992). Preferably, the oligonucleotide used in the methods of the invention are DNA molecules.

The term "digestion" as used herein in reference to the enzymatic activity of a selection enzyme is used broadly to refer both to (i) enzymes that catalyze the conversion of a polynucleotide into polynucleotide precursor molecules and to (ii) enzymes capable of catalyzing the hydrolysis of at least one bond on polynucleotides so as to interfere adversely with the ability of a polynucleotide to replicate (autonomously or otherwise) or to interfere adversely with the ability of a polynucleotide to be transformed into a host cell. Restriction endonucleases are an example of an enzyme that can "digest" a polynucleotide. Typically, a restriction endonuclease that functions as a selection enzyme in a given situation will introduce multiple cleavages into the phosphodiester backbone of the template strands that are digested. Other enzymes that can "digest" polynucleotides include, but are not limited to, exonucleases and glycosylases.

The term "selection enzyme" refers to an enzyme capable of catalyzing the digestion of a polynucleotide template for mutagenesis, but not significantly digesting newly synthesized mutagenized polynucleotide strands. Selection enzymes may differentiate between template and newly synthesized polynucleotides on the basis of modifications to either the parental template polynucleotide or modifications to newly synthesized mutagenized polynucleotides. Selection enzymes suitable for use in the subject invention have the property of selectively digesting the parental strands of heteroduplexes formed between parental strands and the first or second mutagenized DNA strands produced in the linear cyclic amplification reaction step. Examples of selection enzymes include restriction endonucleases and endoglycosylases.

The term "double-stranded mutagenized circular DNA intermediate" as used herein refers to double-stranded circular DNA structures formed by annealing the first mutagenized DNA strand formed in the subject methods to the second mutagenized DNA strand. When a double-stranded mutagenized circular DNA intermediate is transformed into a host cell, host cell enzymes are able to repair nicks (and possible small gaps) in the molecule so as to provide a closed circular double-stranded DNA that corresponds to the original DNA molecule for mutagenesis that has been modified to contain the specific site-directed mutation or mutations of interest.

DETAILED DESCRIPTION OF THE SPECIFIC EMBODIMENTS

The invention provides for, among other things, improved methods for site-directed mutagenesis. The improved methods of site-directed mutagenesis described herein provide for increased efficiency of mutagenesis and the reduced introduction of secondary mutations. The methods of the invention involve the use of pairs of complementary (or partially complementary) mutagenic primers in linear cyclic amplification reactions. The methods of invention require a minimal number of DNA manipulations thereby decreasing the time and cost of obtaining the desired mutants. In many instances, transformants containing DNA constructs with desired mutations may be obtained in a single day (excluding the time to prepare the mutagenic primers).

The methods of the invention may be used to introduce one or more mutations in DNA sequences of interest. The DNA sequences of interest for modification by the subject mutagenesis methods are necessarily part of a circular DNA molecule, i.e., the template molecule. The methods of the invention comprise the steps of annealing a first and second mutagenic primer to the double-stranded circular molecule for mutagenesis. The mutagenic primers are not generally phosphorylated, but may be 5' phosphorylated. As the DNA molecule for mutagenesis is double-stranded, the annealing step is necessarily preceded by a denaturation step. The annealing step is typically part of a cycle of a linear cyclic amplification reaction. After annealing of the mutagenic primers, first and second mutagenized DNA strands are synthesized from the first and second mutagenic primers, respectively. Synthesis of the first and second mutagenized DNA strands takes place during the synthesis phase of a linear cyclic amplification reaction. The first mutagenized DNA strand produced from the synthesis necessarily comprises the first mutagenic primer at its 5' end. Similarly, the second mutagenized DNA strand comprises the second mutagenic primer. The linear cyclic amplification reaction may be repeated through several cycles until a sufficiency variety of first and second mutagenized DNA strands are produced for the subsequent manipulations. After the linear cyclic amplification reaction steps, i.e., first and second. mutagenized DNA strand synthesis are completed, the parental template DNA is digested by adding a selection enzyme. The selection enzyme serves to digest parental strand DNA. The parental strand DNA digested may be in the form of heteroduplexes formed between parental strands and the first or second mutagenized DNA strands produced in the linear cyclic amplification reaction step. Additionally, the parental strands digested by the selection enzyme may consist of duplexes formed between parental strands. After the digestion step is completed, the first and second mutagenized DNA strands are annealed to one another so as to produce a double-stranded mutagenized circular DNA intermediate. The double-stranded mutagenized circular DNA intermediates are subsequently used to transform a competent host cell. Transformed host cells may then be isolated as colonies and plasmids, i.e., closed circular DNAs, corresponding to the initial DNA molecules for mutagenesis, but containing the desired site-directed mutation or mutations, may be isolated from the transformed cells.

The previous paragraph has been primarily concerned with use of double-stranded circular DNAs as targets for mutagenesis. A person of ordinary skill in the art may readily modify the procedure so as to provide for site directed mutagenesis of circular single-stranded DNAs. In the case of a single-stranded circular DNA molecule for mutagenesis, only the first mutagenic primer is annealed in the initial step. After the first primer is annealed synthesis of the first mutagenized strand proceeds so as to produce a double stranded circular DNA molecule comprising a first mutagenized DNA strand and the parental single-stranded template. After the formation of the circular double stranded molecule, the method may proceed as described in the previous paragraph.

The methods of the invention employ pairs of mutagenic primers consisting of a first mutagenic primer and a second mutagenic primer. The mutagenic primers are about 20 to 50 bases in length, more preferably about 25 to 45 bases in length. However, in certain embodiments of the invention, it may be necessary to use mutagenic primers that are less than 20 bases or greater than 50 bases in length so as to obtain the mutagenesis result desired. The first and second mutagenic primers may be of the same or different lengths; however, in a preferred embodiment of the invention the first and second mutagenic primers are the same length.

The first and second mutagenic primers contain one or more mutagenic sites, i.e., mismatch locations with respect to the target DNA sequence to be mutagenized. The mutagenic site (or sites) may be used to introduce a variety of mutation types into the DNA sequence for mutagenesis. Such mutations include substitutions, insertions, and deletions. The principle of site-directed mutagenesis with single oligonucleotide primers is well known to the person of ordinary skill in the art, and can be found, for example, in Sambrook et al., *Molecular Cloning: A Laboratory Manual, Second Edition*, Cold Spring, Cold Spring Harbor, N.Y. (1989) and Wu et al., *Recombinant DNA Methodology*, Adademic Press, San Diego, Calif. (1989). This information may be used to design the mutagenic sites in the first and second mutagenic primers employed in the subject methods.

The first and second mutagenic primers of the invention are either completely complementary to each other or partially complementary to each other. Preferably, the first and second mutagenic primers are selected so as to be completely complementary to each other. When the first and second mutagenic primers are partially complementary to each other, the region of complementarity should be contiguous. In embodiments of the invention in which the first and second mutagenic primer are partially complementary to one another, the region of complementarity must be sufficiently large to permit the mutagenic primers to anneal to the DNA molecule for mutagenesis; preferably, although not necessarily, the region of complementarity is at least 50% of the length of the primer (50% of the larger primer when the first and second primer are of different lengths). The mutagenic sites of the first and second mutagenic primers are located in or near the middle of the primer. Preferably, the mutagenic sites are flanked by about 10–15 bases of correct, i.e., non-mismatched, sequence so as to provide for the annealing of the primer to the template DNA strands for mutagenesis. In preferred embodiments of subject methods, the GC content of mutagenic primers is at least 40%, so as to increase the stability of the annealed primers. Preferably, the first and second mutagenic primers are selected so as to terminate in one or more G or C bases. The first and second mutagenic primers for use in the subject invention are optionally 5' phosphorylated. 5' phosphorylation may be achieved by a number of methods well known to a person of ordinary skill in the art, e.g., T-4 polynucleotide kinase treatment. After phosphorylation, the phosphorylated primers must be purified prior to use in the methods of the invention so as to remove contaminants that may interfere with the mutagenesis procedure. Preferred purification methods are fast polynucleotide liquid chromatography (FPLC) or polyacrylamide gel electrophoresis; however, other purification methods may be used. These purification steps are unnecessary when non-phosphorylated mutagenic primers are used in the subject methods.

First and second mutagenized DNA strands are synthesized by a linear cyclic amplification reaction. The exact parameter of each portion of a cycle of the linear cyclic amplification reaction used may vary in accordance with factors such as the DNA polymerase used, the GC content of the primers, DNA concentration, etc. Cycle parameters of concern include the time of each portion of the cycle (denaturation, annealing, synthesis) and temperature at which each portion of the cycle takes place. A person of ordinary skill in the art may obtain guidance in optimizing the parameters of the cyclic amplication reaction step for individual experiments can be found in publications describing PCR. The synthesis phase of the linear cyclic amplification reactions used in the subject mutagenesis methods should proceed for a length of time sufficient to produce first and second mutagenized DNA strands equivalent in length (excluding insertions or deletions in the mutagenic primers) to the circular DNA molecule for mutagenesis. When Pfu DNA polymerase is used to catalyze the linear cyclic amplification reaction, the synthesis phase of the linear cyclic amplification reaction optimally occurs with a temperature range of 60°–68° C.; higher temperatures will result in the unwanted effect of mutagenic primer displacement.

The linear cyclic amplification reaction, i.e., the synthesis reaction, may be catalyzed by a thermostable or non-thermostable polymerase enzyme. Polymerases for use in the linear cyclic amplifcation reactions of the subject methods have the property of not displacing the mutagenic primers that are annealed to the template, thereby producing a mutagenized DNA. strand of essentially the same length as the template from which the newly synthesized strand was derived. Preferably, the polymerase used is a thermostable polymerase. The polymerase used may be isolated from naturally occurring cells or may be produced by recombinant DNA technology. The use of Pfu DNA polymerase (Stratagene), a DNA polymerase naturally produced by the thermophilic archae *Pyrococcus furiosus* is particularly preferred for use in the linear cyclic amplification reaction steps of the claimed invention. Pfu DNA polymerase is exceptionally effective in producing first and second mutagenized DNA strands of the appropriate length for formation of the desired double-stranded mutagenized circular DNA intermediates. Examples of other enzymes that may be used in linear cyclic amplification include, but are not limited to, Taq polymerase, phage T7 polymerase, phage T4 polymerase, *E. coli* DNA polymerase I, Vent™ (New England Biolabs, Beverly Mass.) DNA polymerase, Deep Vent™ DNA polymerase (New England Biolabs, Beverly Mass.), Moloney Murine Leukemia Virus reverse transcriptase, and the like. When the DNA molecule for mutagenesis is relatively long, it may be desirable to use a mixture of thermostable DNA polymerase, wherein one of the DNA polymerases has 5'–3' exonuclease activity and the other DNA polymerase lacks 5'–3' exonuclease activity. A description of how to amplify long regions of DNA using these polymerase mixtures can be found, among other places, in U.S. Pat. No. 5,436,149, Cheng et al., *Proc. Natl. Aca. Sci. USA* 91:5695–9 (1994), and Barnes *Proc. Natl. Aca. Sci. USA* 91:2216–2220 (1994). In order to determine whether or not a given polymerase (or multiple polymerase composition) is suitable for use in catalyzing the sythesis step of the linear cyclic amplification reaction (under a given set of conditions), a simple assay using primers and circular template may be performed so as to determine if primer displacement occurs. Primer displacement may readily be detected by performing the gel electrophoresis anaylsis of the assay mixture.

Linear cyclic amplification reactions as employed in the methods of the invention are preferably carried out with the minimum number of amplification cycles required to produce the desired quantity of first and second mutagenized DNA strands. Preferably the number of cycles in the linear cyclic amplification reaction step is 30 cycles or less, more preferably 20 or less cylces are performed, and even more preferably the number of cylces is between 10 and 20 (inclusive). However, the preferred embodiment of cycles will vary in accordance with the number of mutations sought to be introduced into the DNA molecule for mutagenesis. Generally, the optimum number of reaction cycles will increase with the complexity of mutations to be introduced into the DNA molecule for mutagenesis. The use of a large number of amplification cycles is troublesome because of the introduction of unwanted secondary mutations in the amplified sequences, i.e., mutations other than the intended site-directed mutagenesis target. Many polymerases used in linear cyclic amplification reactions, especially Taq DNA polymerase, have relatively high error rates, thus increasing the number of amplification cycles increases the number of secondary mutations produced. Prior to the invention, large numbers of amplification cycles were required for linear cyclic amplification mutagenesis because of the need to use a relatively low concentration of amplification target. In the past, low concentrations of amplification target were required so that the amount of non-mutagenized product in a reaction mixture was significantly smaller than, the amount of desired mutagenized product produced by linear cyclic amplification reactions, thereby reducing the number of transformants containing non-mutagenized polynucleotides. The subject methods of site-directed mutagenesis enable the use of a comparatively small number of amplification steps because relatively large amounts of template may be used without producing an unacceptably high background of unmutagenized DNA molecules. The digestion step serves to lower the background of unmutagenized DNA molecules. When a low, e.g., 5–10, number of amplification cycles are used in the linear cyclic amplification mutagenesis reaction, the amount of template DNA molecule for mutagenesis should be increased so that a sufficient amount of mutagenized product is produced.

The methods of the subject invention comprise a "digesting" or "digestion" step in which the DNA molecules for mutagenesis, i.e., the parental template strands, are digested by a reaction catalyzed by an enzyme. This enzyme is referred to as a "selection enzyme." In order to employ a parental strand digestion step so as to reduce the parental background in site-directed mutagenesis, a polynucleotide modification step must be employed prior to the parental strand digestion step. In a polynucleotide modification step for use in the subject methods of site-directed mutagenesis, either (1) one or more of the nucleotides of the parental template polynucleotides for mutagenesis are enzymatically (or chemically) modified and the first and second mutagenized DNA strands synthesized during the replication reaction, e.g., the linear cyclic amplification reaction, are not modified or (2) one or more of the nucleotides of the first and second mutagenized DNA strands synthesized during the linear cyclic amplification reaction are enzymatically (or chemically) modified and the nucleotides of the parental template DNA molecules for mutagenesis are not modified. The precise modification reaction step selected for use in a given embodiment of the invention is selected in conjunction with the specific selection enzyme used in the digestion step so that the selection enzyme can digest the parental strand, i.e., the original template polynucleotides, and not significantly digest the newly synthesized first and second mutagenized DNA strands.

The modifying step for use in conjunction with a parental strand digestion step may comprise the process of exposing a DNA molecule for modification to a modifying agent. The modification step may be carried out before the linear cyclic amplification reaction step or during the linear cyclic amplification reaction step. The modifying agent may be a methylase enzyme that catalyzes the methylation of a base within the polynucleotide of interest. Examples of suitable methylases for use in the invention include dam methylase, dcm methylase, Alu I methylase, and the like. The modification reaction may take place in vivo or in vitro. In vivo methylation may be conveniently achieved by propagating poly-nucleotides in cells, either prokaryotic or eukaryotic, that endogenously produce a suitable methylase enzyme. In a preferred embodiment of the invention, in vivo methylation is used to carry out the modification step. The polynucleotide modification step may also be accomplished by synthesizing polynucleotides with nucleotides comprising a modified base, e.g., 6-methyl-ATP, rather than directly modifying a polynucleotide after the polynucleotide has been completely synthesized. When the modification reaction is a methylation reaction and the selection enzyme is a restriction endonuclease that requires methylated bases for activity, the methylation step is preferably performed in vivo. When the selection enzyme is a restriction endonuclease that does not cleave its recognition sequence when the recognition sequence of the enzyme is unmethylated, the modification reaction is preferably a methylation reaction performed in vitro by a polymerase catalyzing the incorporation of methylated nucleotides into a newly synthesized polynucleotide strand. When the selection enzyme used in the digestion step is Dpn I, the modification step is preferably the methylation of adenine to produce 6-methyl adenine (dam methylase) and the methylation reaction preferably takes place in vivo by propagating the DNA for mutagenesis as a plasmid in a suitable prokaryotic host cell.

The digestion step involves the addition of a selection enzyme that is capable of digesting the parental, i.e., nonmutagenized, strands of the DNA molecule for mutagenesis, but does not significantly digest newly synthesized polynucleotides produced during a linear cyclic amplification mutagenesis. By performing the digestion step, the number of transformants containing non-mutagenized polynucleotides is significantly reduced. The parental strand digestion step involves adding a selection enzyme to the reaction mixture after the linear cyclic amplification reaction has been completed. Selection enzymes may be restriction endonucleases or other enzymes that are capable of catalyzing the digestion, e.g., cleavage, of parental strands in a linear cyclic amplification reaction, but do not significantly digest the DNA strands newly synthesized during the linear cyclic amplification reaction step. Restriction endonucleases for use in, the parental strand digestion step are selected so as to be able to cleave the parental strands, but not significantly cleave newly synthesized polynucleotides. The restriction endonuclease selected for use in the digestion step may (1) require a specific modification of the parental strand that is not present on the first and second mutagenized DNA strands synthesized during the linear cyclic amplification mutagenesis reactions or (2) the restriction endonuclease selected for use in the parental strand digestion step may be unable to digest polynucleotides that have been modified in a specific way and the first and second mutagenized DNA strands synthesized during linear cyclic amplification reaction have such a modification (and the parental template polynucleotides, i.e, the DNA molecules for mutagenesis, lack the modification).

Restriction endonucleases are preferred for use as selection enzymes in the digestion step. A preferred selection enzyme for use in the parental strand digestion step is the restriction endonuclease Dpn I, which cleaves the polynucleotide sequence GATC only when the adenine is methylated (6-methyl adenine). Other restriction endonucleases suitable for use in the parental strand digestion step include Nan II, NmuD I, and NmuE I. However, restriction endonucleases for use as selection enzymes in the digestion step do not need to be isoschizomers of Dpn I.

In other embodiments of the invention, the selection enzymes used in the digestion step are not restriction endonucleases. Other enzymes for use as selection enzymes include uracil N-glycosylase. Uracil deglycosylase may be used as a selection enzyme by modifying a DNA molecule for mutagenesis to contain one or more uracil bases rather than thymidine. Uracil incorporation preferably occurs in vivo so that uracil deglycosylase may provide for the digestion of parental strands. Polynucleotides may be modified to as to contain thymidine residues by a variety of methods including DNA synthesis with dUTP as a DNA precursor or the replication of DNA in a dut⁻ ung⁻ strain of E. coli. Polynucleotides comprising uracil bases are sensitive to deglycosylation, i.e., digestion, by uracil N-glycosylase and other enzymes with similar glycosylase activity. The use of uracil N-glycosylase is described, among other places in Kunkel, *PNAS USA*, 82:488–492 (1985).

After the "digestion" step is completed or concurrent with the "digestion" step, i.e., the addition of the selection enzyme, the first mutagenized DNA strands and the second mutagenized DNA strands are annealed to one another so as to produce a double-stranded mutagenized circular DNA intermediate. The formation of double-stranded mutagenized circular DNA intermediate takes place in accordance with conventional principles of nucleic acid hybridization and may be performed under a variety of conditions. Conveniently, the annealing of the first and second mutagenized DNA strands so as to form a double-stranded mutagenized circular DNA intermediate may take place simultaneously with the "digesting" step. The formation of the double-stranded circular DNA intermediates may take place in the same reaction vessel in which the "digesting" and/or the linear cyclic amplification reaction step take place. The process of forming double-stranded mutagenized circular DNA intermediates should proceed for a period of time sufficient to produce a convenient number of double-stranded mutagenized circular DNA intermediates to provide a convenient number of clones in the subsequent transformation steps. Generally, incubation for one to two hours at 37° C. will be sufficient in most embodiments of the invention. However, these time and temperature parameters may be readily varied by the person or ordinary skill in the art so as to take into account factors such as DNA concentration, the GC content of the DNA molecules, etc.

After the double-stranded mutagenized circular DNA intermediate formation step is completed, the reaction mixture or a portion thereof, may be used to transform competent single-cell microorganism host cells. It is not necessary to perform a ligation reaction prior to transformation of the host cells. The absence of a ligation step requirement serves to reduce the time and expense required to carry out the methods of the invention as compared with conventional methods of site directed mutagenesis. The host cells may be prokaryotic or eukaryotic. Preferably the host cells are prokaryotic, more preferably, the host cells for transformation are E. coli cells. Techniques for preparing and transforming competent single cell microorganisms are well know to the person of ordinary skill in the art and can be found, for example, in Sambrook et al., *Molecular Cloning: A Laboratory Manual* Coldspring Harbor Press, Coldspring Harbor, N.Y. (1989), Harwood *Protocols For Gene Analysis, Methods In Molecular Biology Vol.* 31, Humana Press, Totowa, N.J. (1994), and the like. Frozen competent cells may be transformed so as to make the methods of the invention particularly convenient.

Another aspect of the invention is to provide kits for performing site-directed mutagenesis methods of the invention. The kits of the invention provide one or more of the enzymes or other reagents for use in performing the subject methods. Kits may contain reagents in pre-measured amounts so as to ensure both precision and accuracy when performing the subject methods. Kits may also contain instructions for performing the methods of the invention. At a minimum, kits of the invention comprise: a DNA polymerase (preferably Pfu DNA polymerase), a selection enzyme (preferably Dpn I), control primers, and control templates. Kits of the invention may contain the following items: individual nucleotide triphosphates, mixtures of nucleoside triphosphates (including equimolar mixtures of dATP, dTTP, dCTP and dGTP), methylases (including Dam methylase), control linear cyclic amplification primers, bacterial strains for propagating methylated plasmids (or phage), frozen competent cells, concentrated reaction buffers, and the like. Preferred kits comprise a DNA polymerase, concentrated reaction buffer, a selection enzyme, a nucleoside triphosphate mix of the four primary nucleoside triphosphates in equimolar amounts, frozen competent cells, control primers, and control templates. The terms "control template" and "control primer" as used herein refer to circular double-stranded DNA molecules and mutagenic primers, respectively that are selected to provide for easily detectable site-directed mutagenesis by the methods of the invention. For example, a control template may comprise a lac Z gene with a point mutation and the control primers may be designed to introduce a site-directed mutation that "repairs" the point mutation. As the lac Z phenotype is easily detected on indicator media, e.g., X-gal, the efficiency of the mutagenesis protocol may be easily monitored.

The invention having been described, the following examples are offered by way of illustrating the invention and not by way of limitation.

EXAMPLES

Control Reactions

A procedure for carrying out the site-directed mutagenesis of plasmid pWhitescript™ 5.7-k.b. is given below. This procedure may be readily adapted for the site-directed mutagenesis of other molecules using different primers. The plasmid pWhitescript™ 5.7-k.b. encodes a mutant lacZ gene with point mutation that produce a lacZ minus phenotype. The primers are designed to "repair" this mutation so as produce a plasmid that gives rise to a lacZ positive phenotype in E. coli grown on indicator medium. Accordingly, pWhitescript™ 5.7-k.b. may be used as a control template in the kits of the invention.

Setting Up the Reactions

1. Synthesize two complementary oligonucleotides containing the desired mutation, flanked by normal nucleotide sequence, i.e., first and second mutagenic primers. Optionally, the primers are 5' phosphorylated and gel purified prior to use in the following steps.
2. Prepare the control reaction as indicated below:

5 µl of 10×reaction buffer

3 µl (3 ng, 0.001 nM) of pWhitescript™ 5.7-k.b. control template (1 ng/µl)

1.25 µl (125 ng, 22 nM) of oligonucleotide control primer #1 [34-mer (100 ng/µl)]

1.25 µl (125 ng, 22 nM) of oligonucleotide control primer #2 [34-mer (100 ng/µl)]

1 µl of 10 mM dNTP mix (2.5 mM each NTP)

Double-distilled water (ddH₂O) to a final volume of 50 µl

Then add:

1 µl of native Pfu DNA polymerase (2.5 U/µl)

3. Prepare the sample reaction(s) as indicated below:
   A series of sample reactions using various concentrations of dsDNA template ranging from 2 to 8 ng (e.g., 2, 4, 6 and 8 ng of dsDNA template) should be set up in order to determine the optimum amount.
   5 μl of 10×reaction buffer
   2–8 ng of dsDNA template
   125 ng of oligonucleotide primer #1
   125 ng of oligonucleotide primer #2
   1 μl of 10 mM dNTP mix (2.5 mM each NTP)
   ddH$_2$O to a final volume of 50 μl
   Then add:
   1 μl of native Pfu DNA polymerase (2.5 U/μl)
3. Overlay each reaction with 30 μl of mineral oil.

TABLE I

Circular Site-Directed Mutagenesis Cycling Parameters

| Segment | Cycles | Temperature | Time |
|---|---|---|---|
| 1 | 1 | 95° C. | 30 Seconds |
| 2 | 10-16 | 95° C. | 30 Seconds |
|  |  | 50° C. | 1 minute |
|  |  | 68° C. | 2 minutes/kb of plasmid length |

Cycling the Reactions and Digesting the Products

1. Thermal cycle each reaction using the cycling parameters are outlined in Table I.
2. Repeat segment 2 of the cycling parameters 10–16 times, depending on the type of mutation desired (i.e., 10 cycles for point mutations, 12 cycles for single amino acid changes and 16 cycles for multiple amino acid deletions or insertions).
3. Following linear amplification, place the reaction on ice for 2 minutes to cool the reaction to ≦37° C.
   Note In the following digestion step, it is important to insert the pipet tip below the mineral oil overlay when adding the Dpn I restriction enzyme to the reaction tubes.
4. Add 1 μl of the Dpn I restriction enzyme (10 U/μl) directly to each amplification reaction below the mineral oil overlay with a pipet tip.
5. Gently and thoroughly mix each reaction mixture by pipetting the solution up and down several times. Spin down the reaction mixtures in a microcentrifuge for 1 minute and immediately incubate each reaction at 37° C. for 1–2 hours to digest the parental (i.e., the nonmutated) supercoiled dsDNA.

Transforming into *Epicurian Coli* XL2-Blue Ultracompetent™ Cells (available from Stratagene)

The following protocol has been used successfully for transforming *E. coli* with pBluescript®-derived plasmids encoding ampicillin or chloramphenicol resistance. Transformation of kanamycin-resistance-encoding plasmids require a 30- to 45-minute outgrowth after 10-fold dilution of the ultracompetent cells with SOC medium (see Media and Reagent Preparation) between steps 3 and 4 of the transformation protocol described in Sambrook et al., *Molecular Cloning: A Laboratory Manual, Second Edition*, Cold Spring Harbor Press, Cold Spring Harbor, N.Y. (1989). Other selections may require a number of similar outgrowth periods.

1. Gently thaw the *Epicurian Coli* XL2-Blue™ ultracompetent cells on ice. For each control and sample reaction to be transformed, aliquot approximately 50 μl of the ultracompetent cells to a prechilled Falcons® 2059 polypropylene tube.
2. Add 1 μl of the Dpn I-treated DNA from each control and sample reaction to separate aliquots of the ultracompetent cells and swirl gently to mix. Incubate the transformation reactions on ice for 30 minutes, swirling periodically throughout the incubation.
   As an optional step, verify the transformation efficiency of the *Epicurian Coli* XL2-Blue ultracompetent cells by adding 1 μl of the pUC18 control plasmid (0.1 ng/μl) to a 50 μl aliquot of the ultracompetent cells and incubating as indicated above.
3. Heat pulse the transformation reactions for 45 seconds at 45 seconds at 42° C. and then place the reactions on ice for 2 minutes. This heat pulse has been optimized for the Falcon 2059 polypropylene tubes.
4. Immediately plate the transformation reactions as outlined below:
   a. Plate the entire volume of the control transformation reaction and only 5 μl of the pUC18 control transformation reaction (if performed) on LB-ampicillin-methicillin agar plates (see *Media and Reagent* section below) that have been spread with 20 μl of 10% (w/v) X-gal and 20 μl of 100 mM IPTG.
   Note: Do not mix IPTG and X-gal, since these chemicals will precipitate. X-gal should be prepared in dimethylformamide (DMF) and the IPTG should be prepared in filter-sterilized dH$_2$O.
   b. Plate the entire volume of each sample transformation reaction on agar plates containing the appropriate antibiotic that is conferred by the plasmid vector being transformed.
5. Incubate the transformation plates at 37° C. for >16 hours.

The expected colony number should be at least 50 colonies. Greater than 80% of the mutagenized control colonies should contain the mutation and appear as blue colonies on agar plates containing IPTG and X-gal.

The mutagenesis efficiency (ME) for the pWhitescript 5.7-kb control template is calculated by the following formula:

$$ME = \frac{\text{Number of blue colony forming units}(cfu)}{\text{Total number of colony forming units}(cfu)} \times 100\%$$

| MEDIA AND REAGENTS | |
|---|---|
| TE Buffer | 10X Reaction Buffer |
| 10 mM Tris-HCl (pH 7.5) | 100 mM KCl |
| 1 mM EDTA | 60 mM (NH$_4$) 2SO$_4$ |
|  | 200 mM Tris-HCl (pH 8.0) |
|  | 20 mM MgCl$_2$ |
|  | 1% Triton ® X-100 |
|  | 100 μg/ml nuclease-free |
|  | bovine serum albumin |
|  | (BSA) |
| LB Agar (per Liter) | LB-Ampicillin-Methicillin Agar |
| 10 g of NaCl | (per Liter) |
| 10 g of tryptone | (use for reduced |
| 5 g of yeast extract | satellite colony |
| 20 g of agar | formation) |
| Add deionized H$_2$O to a | 1 liter of LB agar |
| final volume of 1 liter | Autoclave |
| Adjust pH to 7.0 with 5 N | cool to 55° C. |
| NaOH | Add 20 mg of filter-sterilized |
| Autoclave | ampicillin |

| MEDIA AND REAGENTS | |
|---|---|
| Pour into petri dishes (~25 ml/100-mm plate) | Add 80 mg of filter-sterilized methicillin<br>Pour into petri dishes (~25 ml/100-mm plate) |
| SOB Medium (per Liter)<br>20.0 g of tryptone<br>5.0 g of yeast extract<br>0.5 g of NaCl<br>Autoclave<br>Add 10 ml of 1 M MgCl$_2$ and 10 ml of 1 M MgS)$_4$/liter of SOB medium prior to use<br>Filter sterilize | SOC Medium (per 100 ml)<br>SOB medium<br>Add 1 ml of a 2 M filter-sterilized glucose solution or 2 ml of 20% (w/v) glucose prior to use<br>Filter sterilize |

INCORPORATION BY REFERENCE

All patents, patents applications, and publications cited are incorporated herein by reference.

EQUIVALENTS

The foregoing written specification is considered to be sufficient to enable one skilled in the art to practice the invention. Indeed, various modifications of the above-described makes for carrying out the invention which are obvious to those skilled in the field of molecular biology or related fields are intended to be within the scope of the following claims.

What is claimed is:

1. A composition for introducing a specific mutation into a circular double-stranded DNA molecule, comprising: a DNA polymerase, a selection enzyme, DMSO, a control circular double-stranded DNA molecule, and control first and second mutagenic primers, wherein the first mutagenic primer comprises a region that is complementary to the second mutagenic primer, wherein the first and second mutagenic primers contain at least one mutation site with respect to the DNA molecule, and wherein the at least one mutation site is located within the region of complementarity between the first and second mutagenic primers.

2. The composition of claim 1, wherein the concentration of DMSO is in the range of 5–10% by volume.

3. A kit for introducing a specific mutation into a circular double-stranded DNA molecule, comprising: a DNA polymerase, a selection enzyme, DMSO, a control circular double-stranded DNA molecule, and control first and second mutagenic primers, wherein the first mutagenic primer comprises a region that is complementary to the second mutagenic primer, wherein the first and second mutagenic primers contain at least one mutation site with respect to the DNA molecule, and wherein the at least one mutation site is located within the region of complementarity between the first and second mutagenic primers.

4. The kit of claim 3, wherein the DMSO is used at a concentration in the range of 5–10% by volume.

5. A method of mutagenizing a selected DNA molecule, wherein the DNA molecule is double-stranded and circular, comprising:

annealing a first mutagenic primer to a first strand of the DNA molecule and a second mutagenic primer to a second strand of the DNA molecule, wherein the first mutagenic primer comprises a region that is complementary to the second mutagenic primer and wherein the first and second mutagenic primers each contain at least one mutation site with respect to said DNA molecule, wherein each of the at least one mutation site is located within the region that is complementary between said first and second mutagenic primers;

synthesizing by means of a linear cyclic amplification reaction a first mutagenized DNA strand comprising the first mutagenic primer and a second mutagenized DNA strand comprising the second mutagenic primer, wherein the first mutagenized DNA strand and the second mutagenized DNA strand may form a double-stranded mutagenized circular DNA intermediate, and wherein DMSO is present during the synthesizing; and digesting the DNA molecule, wherein the digestion is mediated by a selection enzyme.

6. The method according to claim 5, wherein the concentration of DMSO is in the range of 5–10% by volume.

7. The method according to claim 5, wherein the selection enzyme is a restriction endonuclease.

8. The method according to claim 5, wherein the linear cyclic amplification reaction is catalyzed by Pfu DNA polymerase.

9. The method according to claim 5, wherein the first and second mutagenic primers are 5' phosphorylated.

10. The method according to claim 5, wherein the linear cyclic amplification reaction is repeated for less than 20 cycles.

11. The method according to claim 5, wherein the first and second mutagenic primers are completely complementary to each other.

12. The method according to claim 5, further comprising the steps:

annealing the first mutagenized DNA strand and the second mutagenized DNA strand so as to form a double-stranded mutagenized circular DNA intermediate, and transforming a host cell with the double-stranded mutagenized circular DNA intermediate.

* * * * *